United States Patent [19]

Cadmus et al.

[11] Patent Number: 4,886,746

[45] Date of Patent: Dec. 12, 1989

[54] HEAT-STABLE, SALT-TOLERANT MICROBIAL XANTHANASE

[75] Inventors: Martin C. Cadmus; Morey E. Slodki, both of Peoria, Ill.

[73] Assignee: The United States of America as represented by the Secretary of Agriculture, Washington, D.C.

[21] Appl. No.: 192,083

[22] Filed: May 10, 1988

[51] Int. Cl.$^4$ .................. C12P 39/00; C12N 9/42; C12N 1/20; C12R 1/01

[52] U.S. Cl. ..................... 435/42; 435/104; 435/200; 435/209; 435/274; 435/822; 435/829; 435/830

[58] Field of Search ............. 435/274, 42, 104, 200, 435/209, 822, 829, 830

[56] References Cited

U.S. PATENT DOCUMENTS 4,410,625  10/1983  Cadmus ............... 435/42
4,690,891   9/1987  Hou et al. ............ 435/42

FOREIGN PATENT DOCUMENTS 30393  6/1981  European Pat. Off. .

OTHER PUBLICATIONS

M. Rinaudo et al., "Enzymic Hydrolysis of the Bacterial Polysaccharide Xanthan by Cellulase," Int. J. Biol. Macromol. 2: 45-48 (1980) [Chem. Abstr. 92:239, Abstr. 176420a (1980)].

M. E. Slodki et al., "Production and Stability of Xanthan Gums; Xanthanases and Their Applicability," Int. Biores. J. 1: 190-199 (1985).

M. C. Cadmus et al., "Enzymic Breakage of Xanthan Gum Solution Viscosity in the Presence of Salts," Dev. Ind. Microbiol. 26: 281-289 (1985).

M. C. Cadmus et al., "Bacterial Degradation of Xanthan Gum," In Industrial Polysaccharides: Genetic Engineering, Structure/Property Relations and Applications, ed. M. Yalpani, pp. 101-107 (1987).

*Primary Examiner*—Herbert J. Lilling
*Attorney, Agent, or Firm*—M. Howard Silverstein; John D. Fado; Mervin E. Brokke

[57] ABSTRACT

A novel mixed bacterial culture isolated from soil by enrichment culture techniques produces a xanthanase enzyme complex which is stable to 65° C. in the presence of salt. These properties render the heat-stable, salt-tolerant xanthanase useful for in situ degradation of xanthan gum in petroleum recovery fluids and other thickened industrial brines.

1 Claim, No Drawings

HEAT-STABLE, SALT-TOLERANT MICROBIAL XANTHANASE

BACKGROUND OF THE INVENTION

1. Field of the Invention

Xanthan gum is a heteropolysaccharide produced as a fermentation product by *Xanthomonas compestris*, a microorganism causing vascular disease of cabbages, cauliflower, and rutabagas. Its structure consists of a linear backbone of β-(1→4)-linked D-glucose residues (linked as in cellulose), which has three-unit-long side chains appended on alternate residues. D-Mannose residues directly appended to the backbone bear D-acetyl substituents on the C-6 position. Pyruvic acetal, i.e., 4,6-O-(1-carboxyethylidene), substituents are on the terminal D-mannosyl residues of some of these side chains, their frequency of occurrence depending on the bacterial strain and fermentation conditions.

Xanthan gum has considerable industrial significance and a variety of applications as summarized by A. Jeanes in "Applications of Extracellular Microbial Polysaccharide-Polyelectrolytes: Review of Literature, Including Patents," J. Polym. Sci., Polym. Symp. No. 45, pp. 216–221 (1974). The stability of its rheological properties under diverse chemical conditions accounts in part for its versatility. For example, the gum is an effective brine thickener for use in drilling mud compositions and also in the secondary and tertiary recovery of petroleum. High-viscosity solutions are employed to carry proppage to fractured rock formations in oil bearing strata. Viscosity is then reduced and the proppage remains to allow better passage of natural gas and petroleum in underground formations in which the temperature often exceeds 50° C. It is essential that an enzymic viscosity breaker for xanthan gum-based hydraulic fluids function under conditions of elevated temperature and salinity. A detailed description of its role in oil recovery is given by Wernau in U.S. Pat. No. 4,119,546.

2. Description of the Prior Art

While the literature is replete with reports on the production, characterization, properties, and applications of xanthan gum, there is a paucity of information on its biological degradation. M. Rinaudo et al. [Chem. Abstr. 92: 176420a (1980)] investigated the mechanism of enzymic hydrolysis by a cellulase. In salt-free solution, a random breakdown of the main chain was observed when the polysaccharide was in the unordered conformation. However, there was no hydrolysis of the more commonly occurring, ordered or helical conformation.

Cripps et al. [Eur. Pat. Appl. 30,393; Chem. Abstr. 95(258): 146157q (1981)] described isolation of a *Corynebacterium sp.* (NCIB 11535) from a soil enrichment culture on xanthan gum as sole carbon source. The extracellular xanthanase produced aerobically by the organism during growth in the presence of xanthan gum also depolymerized carboxymethyl cellulose. At least nine reaction products were detected by thin-layer chromatography after native xanthan gum in distilled water was incubated with the Cripps enzyme at 30° C. Only four products were obtained from the deacetylated polysaccharide, and these were characterized. In addition to D-mannose and its pyruvic acetal, two were shown by compositional and methylation analyses, and by analogy with the known structure of xanthan gum, to be linear oligosaccharides shown below:

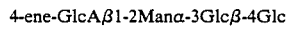

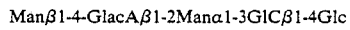

Light absorbance at 232 nm and a positive thiobarbituric acid test suggested that the tetrasaccharide was terminated by an unsaturated (4-ene-) glucuronic acid residue formed through action of a lyase. Presence of two glucose residues in both of the linear oligosaccharides indicated that the hydrolase component of the enzyme complex attacked β-(1→4)-glucosyl linkages to the glucosyl residues bearing side chains.

Although the corynebacterial xanthanase of Cripps showed activity at 70° C, it did not have good thermal stabiliyt; 305 of the activity was lost in 1 hr at 30° C.

Salt-tolerant bacteria that produces a xanthanase complex functional in the presence of brines have been isolated on enrichment culture with xanthan gum as the main carbon source [M.C. Cadmus et. al., "Biodegradation of Xanthan Gum by Vacillus sp.," Appl. Environ. Microbiol. 44: 5 (1982); and U.S. Pat. No. 4,410,625]. It is further noted that the enzyme complex displayed resistance to thermal inactivation at 48° C. in the presence of 4–10% NaCl [M.C. Cadmus et. al., "Enzymic Breakage of Xanthan Gum Solution Viscosity," Dev. Ind. Mcirobiol. 26: 281 (1985)]. In many rock formations, however, the temperature exceeds 60° C., and a more heat-stable enzyme is required.

SUMMARY OF THE INVENTION

We have now discovered a xanthanase-producing microbial mixed culture which demonstrates the capacity to elaborate heat-stable, salt-tolerant extracellular enzymes that degrade xanthan gum in both its ordered and unordered conformations. This mixed culture has been deposited in the ARS Culture Collection in Peoria, IL, under the Accession No. NRRL B-18445. Exoenzymes produced by this mixed culture are functional up to 65° C. in the presence of salts.

In accordance with this discovery, it is an object of the invention to provide a means for biochemically degrading xanthan gum.

It is also an object of the invention to produce relatively high yields of heat-stable, salt-tolerant xanthanases by a commercially feasible fermentation process.

Another object of the invention is to produce xanthanases which are tolerant to the diverse conditions of xanthan utilization.

Other objects and advantages of this invention will become readily apparent from the ensuing description.

DETAILED DESCRIPTION OF THE INVENTION

The mixed bacterial culture of this invention, NRRL B-18445, was originally isolated from soil by enrichment techniques. Nutrient media for enrichment may be any suitable nutrient media containing xanthan as the primary carbon source. Typical nutrient media for enrichment comprise xanthan, 0.2–0.35%; ammonium sulfate, 0.02–30.08%; yeast extract, 0.015–0.03%; tryptone, 0.015–0.03%; sodium chloride, 2–4%; and potassium phosphate buffer, 0.015–0.03 M. The preferred medium for optimum enrichment is set forth in Table I, below.

TABLE I

| | % w/v |
|---|---|
| Xanthan | 0.25 |

TABLE I-continued

|  | % w/v |
|---|---|
| (NH4)2SO4 | 0.05 |
| Yeast extract | 0.025 |
| Tryptone | 0.025 |
| NaCl | 3.0 |
| Potassium phosphate buffer | 0.03 M (pH 6.5) |
| Water | 96.2 |

Soil sampels, 0.25–1.0%, preferably 0.5 g/12 ml were added to the broth and shaken at 42°–46° C., preferably 45° C. until viscosity reduction is observed, typically within 6–10 wks. then two or more additional transfers are completed to conform xanthan biodegredation. The mixed culture is stored on agar slants or in lyophilized form or in liquid broths. Liquid broth storage is preferred for routine experiments because cell growth may be achieved in a shorter period of time than with the other methods.

Enzyme production is accomplished by incubation in the same medium as used in the enrichment broth except that levels of xanthan and sodium chloride are reduced. The preferred levels are NaCl, 2%; xanthan, 0.15%. The mixed culture required for enzyme production may be grown in multiple stages, preferably a minimum of three.

The incubation of the mixed culture is preferably conducted in the temperature range of 40°–48° C. and at an initial pH in the range of about 6.0 to about 7.0, and preferably at a temperature of 45° C. and a pH of 6.4. Under these conditions, the xanthan in a production batch is completely fermented in 3–4 days by which time the pH has typically risen between about 0.1 to 1.0 pH units. Below 45° C., the xanthanase yield diminishes. It is envisioned that pH's as low as about 5.5 can be employed without significant effect on the production or stability of the xanthanase. The fermentation is aerobic and the requisite air flow rate will depend upon factors such as vessel capacity and design, batch size, and the specific culture mixture. Guided by growth rates and xanthanase yields, the optimum rate can be readily determined by the skilled artisan. When the primary purpose of the fermentation is the in situ degradation of the xanthan gum, without recovery of the enzyme, optimization of the culture conditions is not of paramount consequence. However, when the enzyme yield is to be maximized, it is necessary to control the conditions within the aforementioned ranges.

A crude enzyme preparation can be isolated from the fermentation broth by removal of cells such as by centrifugation or filtration. If desired, the enzyme in the supernatant can then be concentrated by dialysis or other conventional means. One or more passes of the crude concentrate on a chromatographic column is effective for obtaining a substantially pure product. While the specific activity of the crude concentrate will typically be on the order of about 200 enzyme units/mg., the chromatographic treatment will result in specific activities of about 680 units/mg. Activities of preparations considered to be substantially pure for purposes of the invention will range between about 600 and 800 units/mg. An enzyme unit is defined as the number of milligrams per 100 ml. of reducing sugar (calculated as D-mannose) liberated per milliliter of enzyme from xanthan in 1 hr at 45° C. and at pH 5.8.

Heat-stable, salt-tolerant xanthase is highly stable during routine handling and purification at room temperatures. About 95% of the activity remains after lyophilization and 90% remains after freezing the concentrate (−20°). There is no loss of activity in solutions stored up to 6 mo at 4° C. under toluene. At 45° C. and in buffer of low ionic strength, activity gradually diminishes to 20% of the maximum after 7 days.

Table II depicts the results of temperature studies conducted in media of relatively low ionic strength. It can be seen that the previously reported salt-tolerant xanthanase [Cadmus et al., Appl. Environ. Microbiol., supra] is stable only to about 40° C. when heated for 20 min. with no activity remaining at 50° C. In contrast, the heat-stable xanthanase is stable to 60° C. when tested under the same conditions. The enzyme(s) were inactivated at 70° C.

TABLE II

| Heat Stability of Heat-Stable, Salt-Tolerant Xanthanase | | | | | | |
|---|---|---|---|---|---|---|
| | Temperature (°C.) | | | | | |
| | 35 | 40 | 45 | 50 | 55 | 60 | 65 |
| | Activity (% of maximum) after 20 min | | | | | | |
| Salt-tolerant xanthase | 100 | 90 | 50 | 0 | 0 | 0 | 0 |
| Heat-stable, salt-tolerant xanthase | 100 | 100 | 100 | 100 | 100 | 95 | 70 |

Salts were previously shown to increase the stability of salt-tolerant xanthanase [Cadmus et al., Dev. Ind. Microbiol., supra]. Table III illustrates the effect of salt on the stability of heat-stable, salt-tolerant xanthanase. In the absence of salt, activity begins to deteriorate above 55° C., while in the presence of 3% sodium chloride the xanthanase dose not begin to lose activity until the temperature exceeded 60° C. At 65° C., 82% of the maximum activity remains after 20 min.

TABLE III

| Effect of Salt on Thermal Stability of Heat-Stable, Salt-Tolerant Xanthase | | | | | |
|---|---|---|---|---|---|
| | Temperature (°C.) | | | | |
| | 50 | 55 | 60 | 65 | 70 |
| | Activity (% of maximum) after 20 min. | | | | |
| No salt | 100 | 100 | 80 | 40 | 10 |
| 3% NaCl | 100 | 100 | 100 | 82 | 20 |

To measure stability to pH, samples were tested over the pH range of 4 to 9 at 25° C. for 24 hr. There is good stability from pH 5 to 8 with optimum stability at pH 5.8. The enzyme is more stable at the basic end of the pH range. At pH 9, 70% of the maximum activity remained, whereas only 105 remained at pH 4.5.

Heat-stable, salt-tolerant xanthanase activity, measured as reducing power release, was determined over a temperature range of 35°–70° C. in the buffere-substrate solution (pH 6.0). THe optimum temperature for xanthan degradation is found to be 50° C. with about 10% reduction at 45° C. and 58°C. For assays and substrate conversions of long duration, 45° was used to ensure a longer period of activity. At this temperature, reaction mixtures remain active for several days.

Tests for optimum pH of activity were carried out over the range of 4–9. Heat-stable, salt-tolerant xanthanase is most active at the pH of maximum stability; i.e., pH 5.8; activity drops sharply below pH 4.8 and above pH 6.5.

Heat-stable, salt-tolerant xanthanase activity may be measured by loss of viscosity and release of reducing power which occur inversely. Product formation during the first 60 min is most rapid, accounting for about 6% conversion of substrate in terms of total carbohydrate content.

The amount of sodium chloride that heat-stable, salt-tolerant xanthanase tolerates is shown in Table IV. Enzymic analyses were performed using salt concentrations up to 105. Activity gradually diminishes over that range with 40% of the maximum activity still remaining in 10% salt. Magnesium and calcium chlorides were also tested at 1% concentrations; neither of these salts affected enzyme activity.

TABLE IV

| Salt Tolerance of Heat-Stable, Salt-Tolerant Xanthanase | | | | | | |
|---|---|---|---|---|---|---|
| NaCl (g/100 ml) | 0 | 2 | 4 | 6 | 8 | 10 |
| Activity (% of maximum) | 100 | 75 | 60 | 50 | 45 | 40 |

Heat-stable, salt-tolerant xanthanase is defined in this invention as a single enzyme or a complex of enzymes capable of degrading xanthan gum. Without desiring to be bound to any particular theory of operation, it is believed that, based upon structural characteriztion of degradation products, at least two enzymes are involved in the heat-stable, salt-tolerant xanthanase: a lyase that removes terminal pyruvated D-mannose residues and a $\beta$-(1→4)-D-Glucanase that cleaves glycosidic linkages of backbone chain residues bearing side chains.

Heat-stable, salt-tolerant xanthanases may be useful in tailoring the viscosity of suspensions for a particular use, such as thinning suspensions prior to injection into underground oil-bearing formations. In addition to increasing the rate of biodegradation, several potential uses for these xanthanases can be envisioned. Isolated enzymes can alter xanthan and related polysaccharide structures for subsequent chemical or biological modifications. The enzymes might also be used to confirm existing xanthan structures and possibly to show a certain specificity for related polysaccharides produced by different species of microorganisms.

The following examples are intended only to further illustrate the invention and are not intended to limit the scope of the invention which is defined by the claims.

EXAMPLE 1

Enrichment Cultures

A mixed bacterial culture (NRRL B-18445) was isolated by enrichment from soil. The enrichment broth consisted of xanthan, 0.25%; $(NH_4)_2SO_4$, 0.05%; yeast extract, 0.025%; tryptone, 0.025% NaCl, 3%; and 0.03 M potassium phosphate buffer (pH 6.5). Soil samples were added to the broth in Erlenmeyer flasks (0.5 g/12 ml) and shaken at 45° C. until viscosity reduction was observed (6-10 wks). After two additional transfers were completed to confirm xanthan biodegradation, the positive culture was streaked on agar medium similar to the enrichment broth except that xanthan and NaCl were reduced to 0.2 and 1.0%, respectively. Neither single colony isolates nor pairs of isolates degraded the polysaccharide.

The mixed culture was stored on agar slants and in lyophilized or liquid broths. The broth was most satisfactory for routine experiments as cell growth and viscosity reduction occurred in 1-3 days vs 2-3 wks when started from agar slant or lyophil cultures.

EXAMPLE 2

Enzyme Production

Stock cultures were maintained by incubation in enrichment broth for 3-4 days at 45° C. and stored in capped vials for up to 6 mo. The same medium was used in the production flasks except that the NaCl level was reduced to 2% and xanthan to 0.15%. The first-stage flask was inoculated with 10% v/v from the stock broth and incubated 3-5 days until viscosity diminished and cell growth became evident. The inoculum flask (second stage) was seeded with 5% v/v from the first stage. After 72 hr, 12 ml of the second stage was inoculated into Fernbach flasks containing 750 ml of medium. Maximum enzyme production was achieved in 42 hr in flasks shaken (150 rpm) at 45° C. Longer incubation diminished activity.

EXAMPLE 3

Enzyme Recovery

Fermentation broth from the mixed culture was clarified by centrifugation (20,000 x g, 20 min, 4° C.) and then concentrated up to 20-fold in an Amicon TCF-10 membrane dialysis apparatus equipped with a PM30 membrane or nominal 30,000 molecular weight cutoff. The concentrate was recentrifuged and dialyzed against 0.02 M potassium phosphate bufer (pH 6.0) for 48 hr to remove excess salts.

The enzyme concentrate was applied to a Sepharose 4B (Pharmacia) column (1.5×150 cm) equilibrated with the above buffer (15 ml/min) at room temperature. All of the axanthanase activity was recovered in the first protein peak. Specific activity increased from 195 units/mg protein (crude) to 680 units/mg protein after this partial purification. Enzyme preparations were stored as either frozen or lyophilized concentrates, or as broths as 4° C. under toluene.

Xanthanase activity was measured as milligrams of mannose equivalents released [Cadmus et al., Appl. Environ. Microbiol., supra] in 100 ml of a buffered-substrate solution containing 0.02 M potassium phosphate (pH 5.8); xanthan gum, 0.18%; $MgSO_4$, 0.01%; $MnSO_4$, 0.002%; and $CaCl_2$, 0.001%. Enzyme (0.5 ml) and buffered substrate (2.0 ml) were equilibrated at 45° C. and mixed. After 60 min, the enzyme was inactivated in boiling water (10 min) prior to measurement of reducing power.

EXAMPLE 4

Product Characterization

Low molecular weight (LMW) products of the enzymatic hydrolysis of Example 3 were separated from high molecular weight (HMW) material by means of a dialysis apparatus equipped with a membrane of nominal 10,000 molecular weight retention. Thin-layer cellulose chromatograph yof the LMW fraction revealed O-acetylated, UV-absorbing oligosaccharide(s) near the origin and a single hexose spot with mobility characteristic of 4,6-O-(1-carboxyethylidene)-D-mannose. Oligosaccharide and pyruvated mannose were separated by column chromatography on Bio-Gel P-2. The oligosaccharide fraction did not contain pyruvic acid and exhibited an absorption spectrum characteristic of unsaturated uronic acid. Methylation analysis of this fraction accorded with a 1:1 mixture of branched oligosaccharides shown below.

Manβ1-4GlcAβ1-2-(Ac-6)Manα1-3(Glcβ1-4)Glc

-ene-GlcAβ1-2-(Ac-6)Manα1-3)(Glocβ1-4)Glc

Prior to methylation, the mixture was carboxy-reduced with NaBD$_4$. In this way, the 2,3,6-tri-O-methyl glucose derived from glucuronic acid residues was identified by mass spectrometry as the 6-d$_2$ compound; the 1-d-1,2,5,6-tetra-O-methyl glucitol derived from di-O-substituted reducing end groups was identified in like manner.

The HMW fragment was O-acetylated, devoid of pyruvic acetal, and gave a UV spectrum similar to that obtained for the LMW products. Methylation analysis again revealed a 3,4-di-O-substituted glucose reducing end group. The data agreed closely with a structure containing three triasaccharide and two unsaturated disaccharide side chains plus two additional unsubstituted main chain (1→4)-linked glucosyl residues; MN~4600, calculated as K$^+$salt.

From the above results, it appears that the heat-stable, salt-tolerant xanthanase consists of two enzymes: a lyase that specifically removed pyruvated mannose residues and a new β-(1→4)-glucanohydrolase that cleaves the linkage between the glucosyl residue bearing the side chain and the succeeding unsubstituted glucosyl residue of the main chain.

It is understood that the foregoing detailed description is given merely by way of illustration and that modification and variations may be made therein without departing from the spirit and scope of the invention.

We claim:

1. A mixed bacterial culture having the identifying characteristics of ARS Culture Collection Accession No. NRRL B-18445; said culture being capable of producing xanthanase enzymes which are functional up to 65° C.

* * * * *

UNITED STATES PATENT AND TRADEMARK OFFICE
CERTIFICATE OF CORRECTION

PATENT NO. : 4,886,746
DATED : December 12, 1989
INVENTOR(S) : Martin C. Cadmus and Morey E. Slodki It is certified that error appears in the above—identified patent and that said Letters Patent is hereby corrected as shown below:

Column 2, line 15, delete "stabiliyt" and insert -- stability -- ;
Column 2, line 15, delete "30S" and insert -- 30% -- ;
Column 2, line 16, delete "produces" and insert -- produce -- ;
Column 2, line 20, delete "*Vacillus*" and insert -- *Bacillus* -- .
Column 3, line 10, delete "sampels" and insert -- samples -- ;
Column 3, line 10, delete "were" and insert -- are -- .
Column 4, line 52, delete "10S" and insert -- 10% -- ;
Column 4, line 55, delete "buffere-substrate" and insert -- buffered-substrate -- .
Column 5, line 8, delete "10S" and insert -- 10% -- .
Column 6, line 26, delete "or" and insert -- of -- ;
Column 6, line 38, delete "as" and insert -- at -- ;
Column 6, line 58, delete "chromatograph yof" and insert chromatography of -- .
Column 7, line 4, delete
"-ene-GlcAβ1-2(Ac-6)Manα1-3)Glocβ1-4)Glc" and insert --
4-ene-GlcAβ1-2(Ac-6)Manα1-3(Glcβ1-4)Glc -- .
Column 8, line 5, delete "removed" and insert -- removes -- .

Signed and Sealed this

Twenty-first Day of July, 1992

*Attest:*

DOUGLAS B. COMER

*Attesting Officer*      *Acting Commissioner of Patents and Trademarks*